United States Patent
Kim et al.

(10) Patent No.: US 9,495,725 B2
(45) Date of Patent: Nov. 15, 2016

(54) METHOD AND APPARATUS FOR MEDICAL IMAGE REGISTRATION

(71) Applicant: Samsung Electronics Co., Ltd., Suwon-si (KR)

(72) Inventors: Jung-bae Kim, Hwaseong-si (KR); Young-kyoo Hwang, Seoul (KR); Do-kyoon Kim, Seongnam-si (KR); Won-chul Bang, Seongnam-si (KR); Young-taek Oh, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 14/163,234

(22) Filed: Jan. 24, 2014

(65) Prior Publication Data
US 2014/0212014 A1 Jul. 31, 2014

(30) Foreign Application Priority Data
Jan. 29, 2013 (KR) ........................ 10-2013-0010100

(51) Int. Cl.
*G06T 7/00* (2006.01)
*G06T 3/00* (2006.01)
*A61B 6/00* (2006.01)

(52) U.S. Cl.
CPC ............ *G06T 3/0068* (2013.01); *G06T 7/003* (2013.01); *A61B 6/5288* (2013.01); *G06T 2207/10072* (2013.01); *G06T 2207/10132* (2013.01)

(58) Field of Classification Search
None
See application file for complete search history.

(56) References Cited

U.S. PATENT DOCUMENTS

| | | | |
|---|---|---|---|
| 7,245,698 B2 | 7/2007 | Pang et al. | |
| 8,111,892 B2 | 2/2012 | Hyun et al. | |
| 2008/0219536 A1* | 9/2008 | Liao et al. | 382/131 |
| 2009/0097778 A1* | 4/2009 | Washburn et al. | 382/294 |
| 2009/0303252 A1* | 12/2009 | Hyun et al. | 345/643 |
| 2010/0067768 A1* | 3/2010 | Ionasec et al. | 382/131 |
| 2011/0160566 A1* | 6/2011 | Petropoulos et al. | 600/411 |
| 2015/0043794 A1* | 2/2015 | Tahmasebi Maraghoosh et al. | 382/128 |

FOREIGN PATENT DOCUMENTS

| | | |
|---|---|---|
| EP | 1127331 B1 | 8/2001 |
| KR | 10-2011-0045319 | 5/2011 |
| KR | 10-1117026 | 2/2012 |

OTHER PUBLICATIONS

Wein et al,, "Automatic CT-ultrasound registration for diagnostic imaging and image-guided intervention." Medical Image Anaylsis. vol. 12, 2008, pp. 577-585.*

Rueckert, Daniel, et al. "Nonrigid Registration Using Free-Form Deformations: Application to Breasr MR Images." *Medical Imaging, IEEE Transactions on* 18.8 (Aug. 1999) pp. 712-721.

* cited by examiner

*Primary Examiner* — Jon Chang
(74) *Attorney, Agent, or Firm* — NSIP Law

(57) ABSTRACT

Disclosed are a method and apparatus for registering images having different modalities. The medical image registration method includes performing, at an initial register, multi-modality registration of a reference image from a plurality of first images captured during a first breathing period and a second image; performing, at the initial register, single-modality registration of the reference image and each of the other first images; generating registration images between the plurality of first images and the second image based on the multi-modality registration and the single-modality registration; acquiring a third image captured after the first breathing period; and detecting an image corresponding to the third image from the registration images.

22 Claims, 7 Drawing Sheets

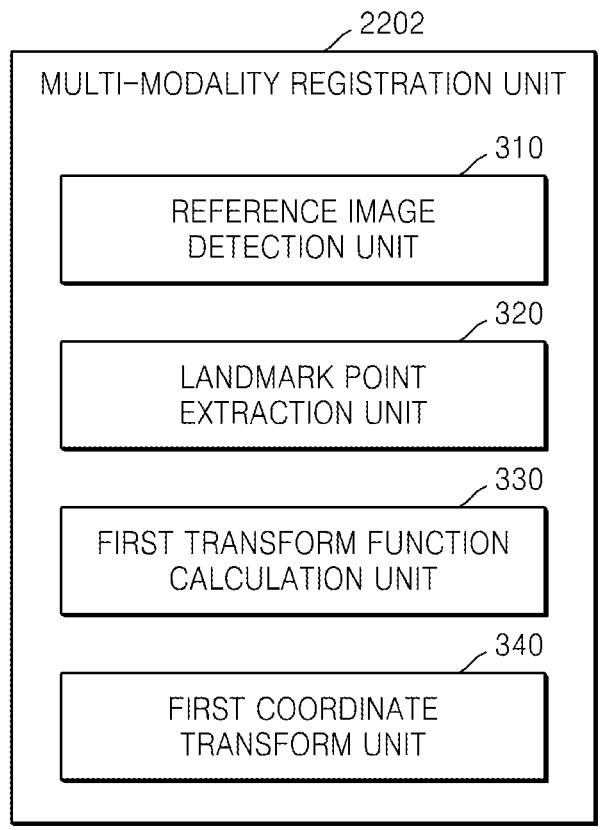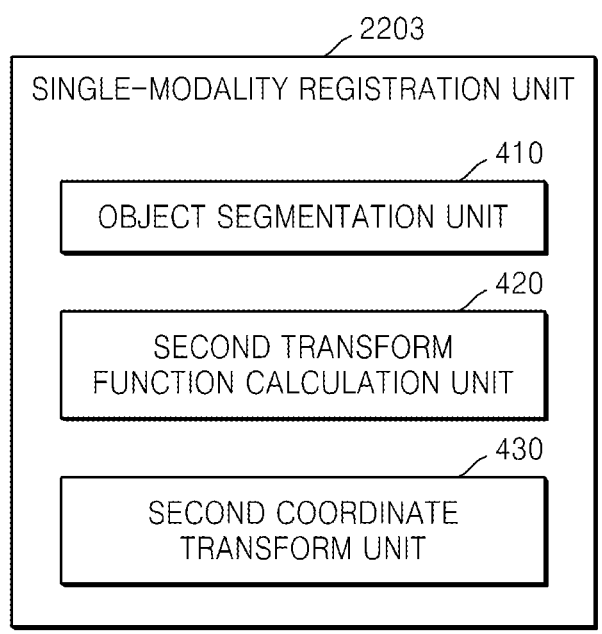

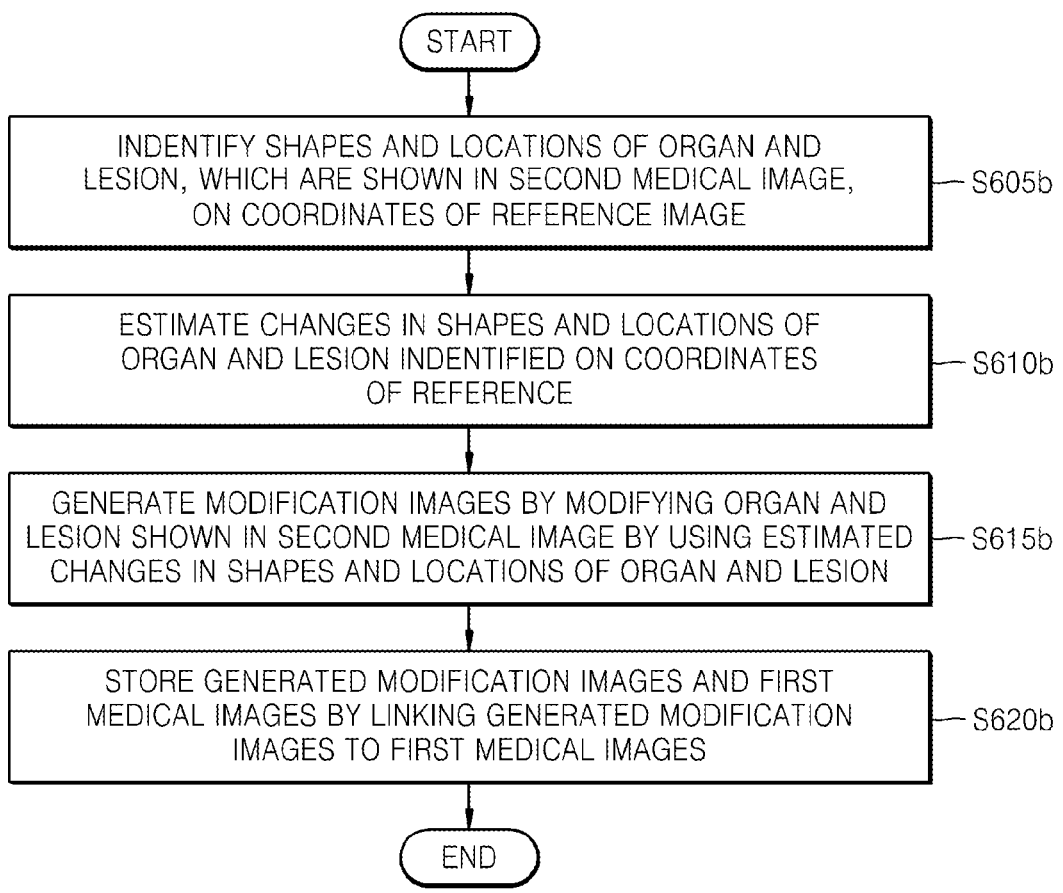

METHOD AND APPARATUS FOR MEDICAL IMAGE REGISTRATION

CROSS-REFERENCE TO RELATED APPLICATIONS

This application claims the benefit under 35 USC §119(a) of Korean Patent Application No. 10-2013-0010100, filed on Jan. 29, 2013, in the Korean Intellectual Property Office, the entire disclosure of which is incorporated herein by reference for all purposes.

BACKGROUND

1. Field

The following description relates to methods and apparatuses for registration a plurality of medical images by considering physical activities of a subject.

2. Description of Related Art

Recently it has become possible to obtain high-resolution medical images and it has become possible to conduct minute operation with medical equipment. For example, technology for treating the human body while observing the inside of the human body with a medical image device by making a small hole in the skin and directly inserting a catheter or a medical needle into a blood vessel of a desired part of the human body without a direct incision on the human body has been developed. This is called "a procedure using images" or "an interventional imaging procedure." A medical practitioner perceives a location of an organ or a lesion through an image. A subject breathes or moves during a procedure, thus, the medical practitioner needs to perceive a change due to the breathing or movement of the subject. Thus, the medical practitioner is supposed to perform the procedure by accurately and quickly perceiving the breathing or movement of the subject based on real-time images. However, it is not easy to perceive a shape of the organ or the lesion with the naked eyes on the real-time images. Compared with ultrasound images, organs and lesions may be clearly identified from magnetic resonance (MR) or computed tomography (CT) images. However, since the MR or CT images cannot be acquired in real-time during a medical procedure, the breathing and movement of a subject, which occur during the medical procedure, are not reflected in the images observed by the medical practitioner.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided an image registration method including performing, at an initial register, multi-modality registration of a reference image from a plurality of first images captured during a first breathing period and a second image; performing, at the initial register, single-modality registration of the reference image and each of the other first images; generating registration images between the plurality of first images and the second image based on the multi-modality registration and the single-modality registration; acquiring a third image captured after the first breathing period; and detecting an image corresponding to the third image from the registration images.

The image registration method may include outputting the detected image.

The generating of the registration images may include modifying anatomical information included in the second image to correspond to different breathing states of the other first images based on the single-modality registration; and adding the modified anatomical information to the other first images.

The detecting of the image corresponding to the third image may include detecting an image having the highest similarity with the third image from the plurality of first images; and outputting the detected image may include outputting anatomical information added in the registration image corresponding to the detected image from the plurality of first images.

The performing of the multi-modality registration may include performing rigid registration or affine registration of the reference image and the second image, and the performing of the single-modality registration may include performing non-rigid registration of the reference image and the other first images.

The performing of the multi-modality registration may include extracting landmark points from each of the reference image and the second image; and rotating, scaling, translating, or shearing any one of the reference image and the second image based on the other image and the extracted landmark points.

The performing of the single-modality registration may include estimating a displacement and a deformation of an organ or a lesion for the first breathing period by using brightness information and gradient information between the reference image and each of the other first images.

The reference image may be an image that has been captured in a breathing state most similar to a breathing state in which the second image has been captured.

The generating of the registration images may include identifying a shape and a location of an organ or a lesion, which are shown in the second image, on coordinates of the reference image by using the multi-modality registration; and estimating changes in the shape and the location of the organ or the lesion indentified on the coordinates of the reference image with each of the other first images by using the single-modality registration.

The image registration method may include storing information about the estimated changes in the shape and location of the organ or the lesion by linking the information to the first images.

The generating of the registration images further may include generating modification images by modifying the organ or the lesion shown in the second image to correspond to the first images by using the estimated shape and location of the organ or the lesion; and storing the first images and the modification images by linking the other first images to the modification images.

In another general aspect, there is provided an image registration apparatus including a multi-modality register configured to register a reference image from a plurality of first images captured during a first breathing period and a second image; a single-modality register configured to register each of the other first images and the reference image; a database (DB) constructor configured to generate registration images between the plurality of first images and the second image based on results of the multi-modality register and the single-modality register; and a register configured to acquire a third image captured after the first breathing period and to detect an image corresponding to the third image from the registration images.

The DB constructor may be further configured to modify anatomical information shown in the second image to correspond to different breathing states of the other first images based on the single-modality registration result and to add the modified anatomical information to the other first images.

The register may be further configured to detect an image having the highest similarity with the third image from the plurality of first images and to output anatomical information added in the image having the highest similarity with the third image from the registration images.

The multi-modality register may be further configured to perform rigid registration or affine registration of the reference image and the second image, and the single-modality register is further configured to perform non-rigid registration of the reference image and the other first images.

The multi-modality register may be further configured to extract landmark points from each of the reference image and the second image, and to rotate, scale, translate, or shear any one of the reference image and the second image based on the other image and the extracted landmark points.

The single-modality register may be further configured to estimate a displacement and a deformation of an organ or a lesion for the first breathing period by using brightness information and gradient information between the reference image and each of the other first images.

The multi-modality register may be further configured to detect the reference image as an image that, has been captured in a breathing state most similar to a breathing state in which the second image has been captured.

The DB constructor may be further configured to identify a shape and a location of an organ or a lesion, which are shown in the second image, on coordinates of the reference image by using the multi-modality registration result and to estimate changes in the shape and the location of the organ or the lesion indentified on the coordinates of the reference image with each of the other first images by using the single-modality registration result.

The DB constructor may be further configured to store information about the estimated changes in the shape and the location of the organ or the lesion by linking the information to the first images.

The DB constructor may be further configured to generate modification images by modifying the organ and the lesion shown in the second image to correspond to the first images by using the estimated shape and the location of the organ or the lesion and to store the first images and the modification images by linking the other first images to the modification images.

The third image may be acquired in real-time.

A image acquirer may be configured to acquire the plurality of first images captured during the first breathing period and the second image of a subject.

The image acquirer may be further configured to acquire the third image captured after the first breathing period.

In another general aspect, there is provided an image registration method including acquiring, at an image acquirer, a plurality of first images captured during a first breathing period and a second image; detecting a reference image from the plurality of first images, wherein the reference image has been captured in a breathing state most similar to a breathing state of the second image; extracting landmark points from each of the reference image and the second image, and rotating, scaling, translating, or shearing any one of the reference image and the second image based on the other image and the extracted landmark points; estimating a shape and a location of an organ or a lesion for the first breathing period based on the difference of brightness information and gradient information between the reference image and each of the other first images; generating a plurality of registration images corresponding to the plurality of first images by modifying organ and lesion of the second image based on the estimated shape and location of the first images; acquiring, at the image acquirer, a third image captured after the first breathing period; detecting an image from the plurality of first images that is most similar to the third image; and outputting the registration image corresponding to the detected first image.

Other features and aspects will be apparent from the following detailed description, the drawings, and the claims.

BRIEF DESCRIPTION OF THE DRAWINGS

FIG. 3 is a diagram illustrating an example of a multi-modality registration unit of the medical image registration apparatus of FIG. 2.

FIG. 4 is a diagram illustrating an example of a single-modality registration unit of the medical image registration apparatus of FIG. 2.

FIG. 6B is a diagram illustrating another example of an operation of generating a set of registration images in the medical image registration method of FIG. 5.

Figure 1:
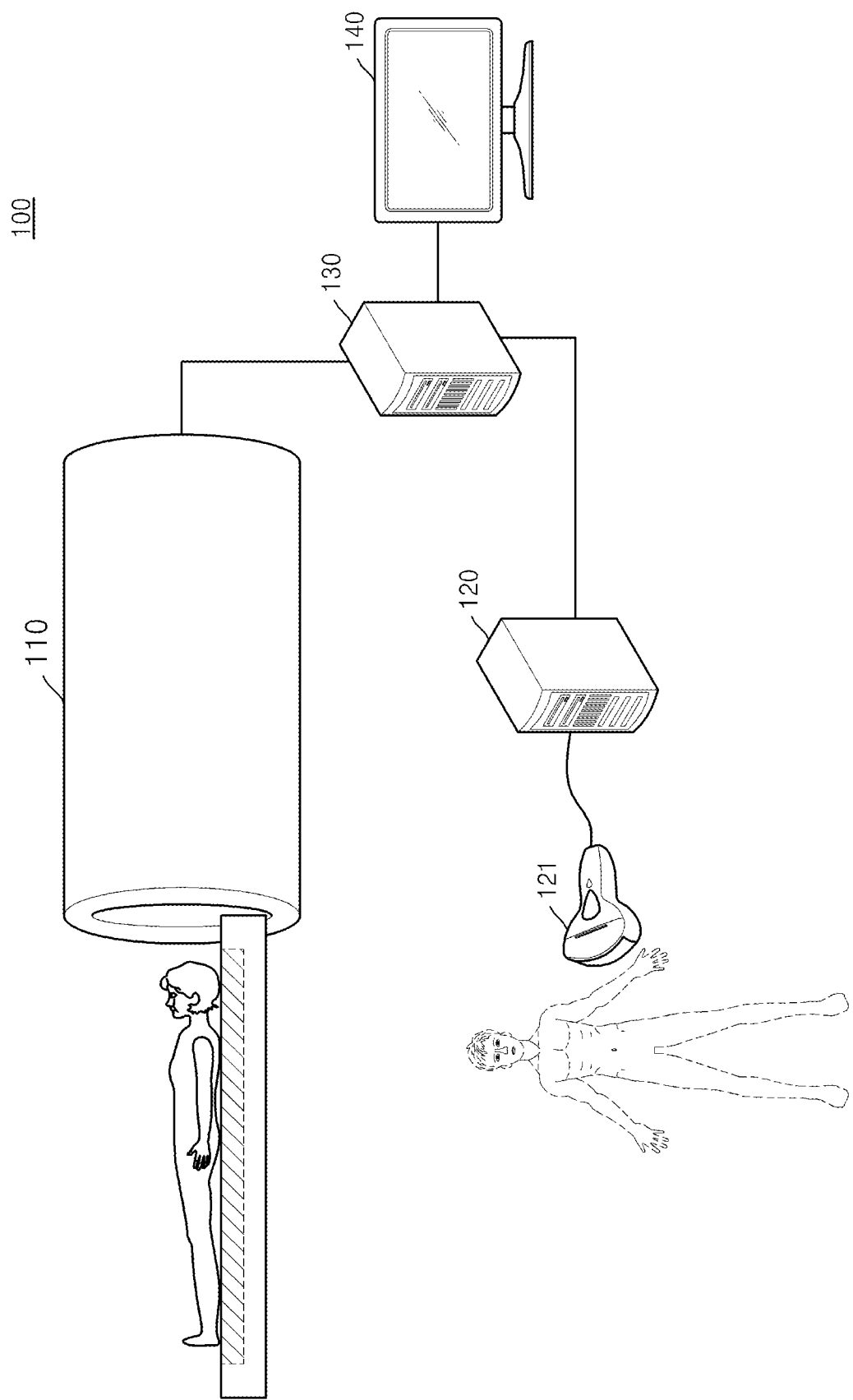
FIG. 1 is a diagram of an apparatus for medical image registration.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

FIG. 1 is a diagram of a system 100. Referring to FIG. 1, the system 100 may include a first medical device 120, a second medical device 110, a medical image registration apparatus 130, and an image display device 140.

The second medical device 110 generates a second medical image for a volume of interest (VOI) of a subject before a medical procedure. For example, the second medical device 110 may include devices, such as, for example, a computed tomography (CT) imaging device, a magnetic resonance (MR) imaging device, an X-ray imaging device, and a positron emission tomography (PET) imaging device. Hereinafter, for convenience of description it is assumed that the second medical image may be an MR or CT image. A location of an organ or lesion may be clearly identified from the MR or CT image generated by the second medical device 110. However, in the MR or CT image, a real-time change of a shape or location of an organ when a subject breathes or turns over during a medical procedure cannot be acquired. Because the image cannot be output in real-time, it is recommended to capture CT images a short time before. Moreover, there is a concern of a long exposure for a subject and a medical practitioner to radioactivity in a capturing method using radiation. In general, CT images are captured when a subject temporarily stops breathing, e.g., in a maximum inhalation state.

The first medical device 120 provides medical images for the VOI of the subject in real-time. Thus, a change in the medical images based on the physical activity of the subject may be observed using the first medical device 120. The first medical device 120 may include an ultrasonography machine for generating real-time images during an interventional medical procedure for a subject. The first medical device 120 irradiates ultrasound signals on a region of interest through a probe 121 disposed in the first medical device 120 and the first medical device 120 generates an ultrasound image by detecting reflected ultrasound signals. The probe 121 may includes a piezoelectric transducer. When ultrasound waves in a range of several MHz to hundreds of MHz are delivered from the probe 121 to a predetermined part inside the body of a subject, the ultrasound waves are partially reflected from layers between different tissues. The ultrasound waves are reflected from parts inside the human body that vary in density, such as, for example, blood cells in blood plasma and small structures in organs. The reflected ultrasound waves vibrate the piezoelectric transducer of the probe 121, and the piezoelectric transducer outputs electrical pulses in response to the vibration. These electrical pulses are transformed into an image.

The first medical device 120 captures a plurality of first medical images during a first breathing period of the subject before the medical procedure. The plurality of first medical images are captured at different time points in the first breathing period. For example, the plurality of first medical images may be captured in maximum inhalation, half inhalation, and maximum exhalation states. In addition, the first medical device 120 captures a third medical image during the medical procedure. For convenience of description, it is assumed that the third medical image is an ultrasound medical image acquired by the first medical device 120. However, it will be understood by one of ordinary skill in the art that the third medical image may be acquired by a medical device other than the first medical device 120.

As described above, medical images acquirable by the first medical device 120, e.g., ultrasound images, may be obtained in real-time, but the ultrasound images include a lot of noise. Thus, it is difficult to identify an outline of an organ, an internal structure, or a lesion from the ultrasound images because contrast of brightness and darkness at an interface between a lesion and surrounding tissue, i.e., edge contrast of an object, is relatively low in the ultrasound images since the lesion and the surrounding tissue have similar ultrasound characteristics. In addition, noise and artifacts due to interference and dispersion of ultrasound waves exist in the ultrasound images. That is, while ultrasound medical images are more quickly acquirable than MR or CT images, the ultrasound medical images have a low signal-to-noise ratio (SNR) and low edge contrast of an object, and thus, an organ and a lesion, which are identified in the MR or CT images, are not clearly identified from surrounding tissue in the ultrasound medical images.

The medical images captured by the first medical device 120 and the second medical device 110 may be three-dimensional medical images generated by accumulating cross-sectional images, which are two-dimensional. For example, the second medical device 110 captures a plurality of cross-sectional images while changing locations and orientations of the cross-sectional images. When the cross-sectional images are accumulated, three-dimensional volume image data representing a predetermined part of the body of a subject may be generated. This method of generating three-dimensional volume image data by accumulating cross-sectional images is called a multiplanar reconstruction (MPR) method. Hereinafter, it is assumed that all images captured by the first medical device 120 and the second medical device 110 are three-dimensional.

The medical image registration apparatus 130 generates a set of registration images by registering the first medical images and the second medical image before the medical procedure. The medical image registration apparatus 130 also registers the third medical image and the generated registration images during the medical procedure.

The registration includes a process of matching coordinates used by the first medical device 120 with coordinates used by the second medical device 110. A registration image may be a fusion image in which different medical images overlap each other or an image in which different medical images are arranged alongside each other. The medical images registered by the medical image registration apparatus 130 may be displayed by the image display device 140.

Figure 2:
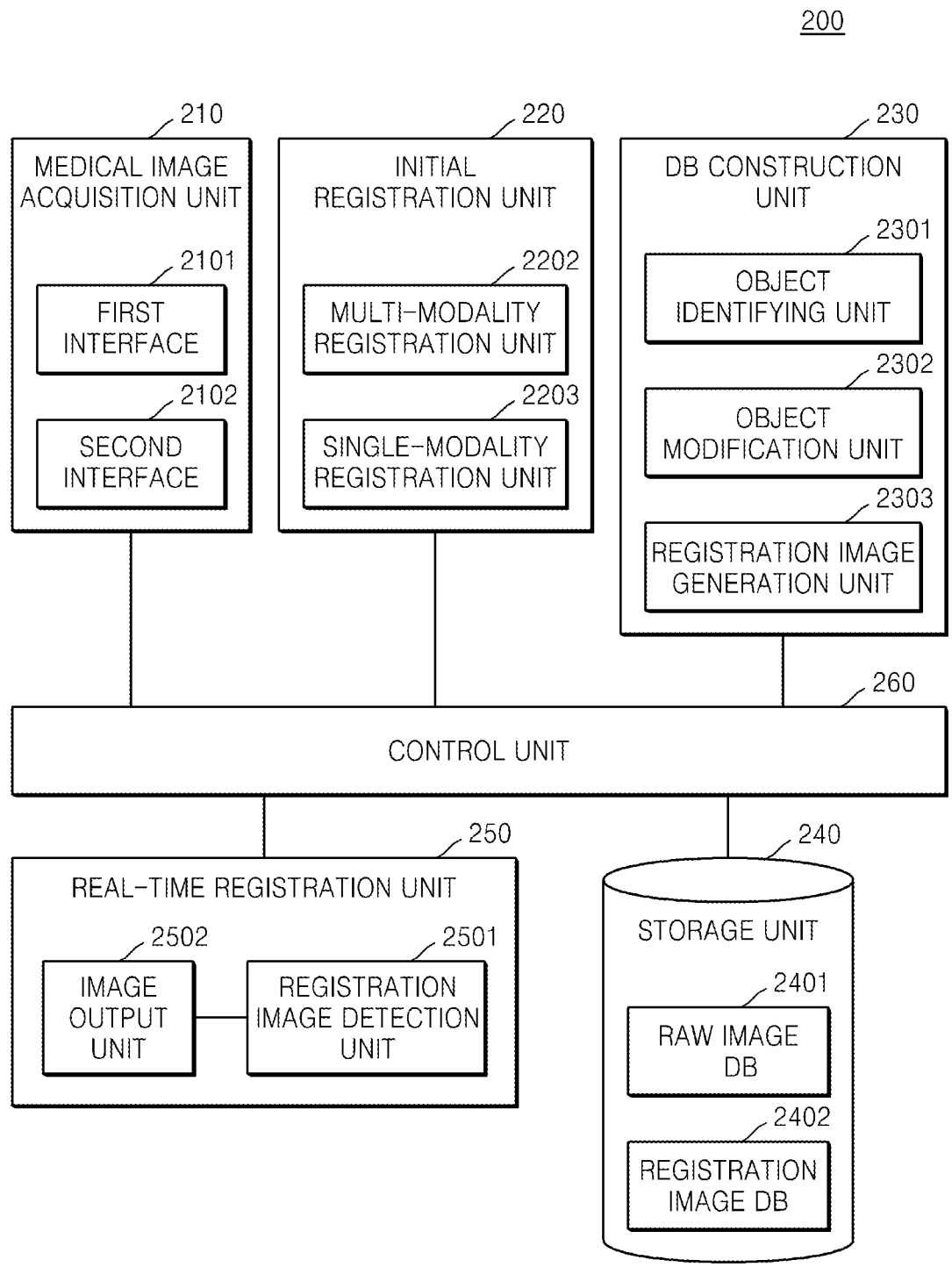
FIG. 2 is a diagram illustrating an example of a medical image registration apparatus.

FIG. 2 is a diagram of a medical image registration apparatus 200. Referring to FIG. 2, the medical image registration apparatus 200 may include a medical image acquisition unit 210, an initial registration unit 220, a database (DB) construction unit 230, a storage unit 240, a real-time registration unit 250, and a control unit 260.

The medical image acquisition unit 210 acquires a plurality of first medical images 550 (refer to FIG. 5) of a subject, which are captured by the first medical device 120 for a predetermined time. The medical image acquisition unit 210 acquires a second medical image 540 (refer to FIG. 5) of the subject, which is captured by the second medical device 110. In addition, the medical image acquisition unit 210 acquires a third medical image 570 (refer to FIG. 5) of the subject, which is captured by the first medical device 120 after the plurality of first medical images 550 are captured. The medical image acquisition unit 210 may include first interface 2101 and second 2102. These interfaces 2101 and 2102 are used to acquire the medical images captured by the first medical device 120 and the second medical device 110, respectively. The first and second interfaces 2101 and 2102 are controlled by the control unit 260. The first and second interfaces 2101 and 2102 may be implemented as one input/output (I/O) interface.

The plurality of first medical images 550 are preferably captured for a first breathing period "t" of the subject. The first breathing period "t" indicates a time length of one period in a periodic breathing process in which the subject repeats inhalation and exhalation. However, it will be understood by one of ordinary skill in the art that the plurality of first medical images 550 may be captured for a time period longer than one period. The plurality of first medical images 550 are captured in different breathing states within the first breathing period "t." For example, when it is assumed that the first breathing period "t" is 1 second, five first medical images 550 may be captured with an interval of 0.2 seconds. Although the plurality of first medical images 550 are preferably captured before a medical procedure of the subject, the plurality of first medical images 550 may be captured even during the medical procedure before the third medical image 570 is captured.

The second medical image 540 is captured in an arbitrary breathing state, such as, for example, maximum inhalation of the subject, and an image which is the same as or very similar to the second medical image 540 exists among the plurality of first medical images 550. Since the plurality of first medical images 550 are captured for the first breathing period "t" including maximum inhalation and maximum exhalation, an image which is the same as or similar to the second medical image 540 captured in maximum inhalation exists among the plurality of first medical images 550.

The third medical image 570 is captured during the medical procedure and is preferably an image of the same modality as the plurality of first medical images 550. The third medical image 570 may be a two-dimensional or three-dimensional ultrasound image captured by the first medical device 120 or a third medical device (not shown) for providing images in real-time during a medical procedure. The third medical image 570 is acquired by the first interface 2101. However, the medical image acquisition unit 210 may further include a third interface (not shown) for acquiring the third medical image 570.

The first, second, and third medical images 550, 540, and 570 acquired by the medical image acquisition unit 210 may be stored in a raw image database 2401 of the storage unit 240. A registration image database 2402 and the raw image database 2401 of the storage unit 240 may be implemented by one or more physical/logical storage medium.

The initial registration unit 220 registers the plurality of first medical images 550 having different modalities and the second medical image 540. The initial registration unit 220 performs multi-modality registration in which a reference image 551 (refer to FIG. 5) from the plurality of first medical images 550 and the second medical image 540 are registered. The initial registration unit 220 may minimize errors in the multi-modality registration and quickly and accurately perform the multi-modality registration by registering only images captured in the same or most similar breathing state for the multi-modality registration.

In addition, the initial registration unit 220 performs single-modality registration in which registration between the plurality of first medical images 550 having the same modality is performed. Even though the initial registration unit 220 registers the plurality of first medical images 550 captured at different breathing time points, the breathing time points at which the plurality of first medical images 550 have been captured are close to each other that the plurality of first medical images 550 can be assumed to have the same modality. Thus, the initial registration unit 220 may quickly and accurately perform the single-modality registration.

The initial registration unit 220 may include a multi-modality registration unit 2202 for performing the multi-modality registration and a single-modality registration unit 2203 for performing the single-modality registration. The multi-modality registration unit 2202 registers the reference image 551 of the plurality of first medical images 550 captured for the first breathing period "t" of the subject and the second medical image 540. The multi-modality registration unit 2202 performs rigid registration or affine registration of the reference image 551 and the second medical image 540. The single-modality registration unit 2203 registers each of the other first medical images 552, 553, and 554 (refer to FIG. 5) acquired at different breathing time points from the reference image 551 and the reference image 551. The single-modality registration unit 2203 performs non-rigid registration of the reference image 551 and the other first medical images 552, 553, and 554. The single-modality registration unit 2203 may estimate displacements and deformations of organs and lesions for the first breathing period "t" by using brightness information and gradient information between the reference image 551 and each of the other first medical images 552, 553, and 554. The gradient information indicates a vector indicating an increase or decrease in a brightness value of voxels of the plurality of first medical images 550.

In terms of image modality, registration is performed by dividing the registration into multi-modality registration and single-modality registration, and in terms of an image capturing time point, registration is performed by dividing the registration into registration in the same breathing state and registration in different breathing states. If single-modality registration of the reference image 551 and the second medical image 540 is performed and if hybrid registration of the registration image according to the single-modality registration and the other first medical images 552, 553, and 554 is performed, registration may be inaccurate in the hybrid registration. This is because the registration image and the other first medical images 552, 553, and 554 are neither captured in the same breathing state nor do they have the same modality.

An example of the multi-modality registration unit 2202 and the single-modality registration unit 2203 will now be described in more detail with reference to FIGS. 3 and 4. Referring to FIG. 3, the multi-modality registration unit 2202 may include a reference image detection unit 310, a landmark point extraction unit 320, a first transform function calculation unit 330, and a first coordinate transform unit 340.

The reference image detection unit 310 detects the reference image 551 from among the plurality of first medical images 550. The reference image detection unit 310 detects the reference image 551 based on similarities between the plurality of first medical images 550 and the second medical image 540. The reference image detection unit 310 detects a reference image 551 from among the plurality of first medical images 550. The reference image 551 is the image that has been captured in a breathing state most similar to a breathing state in which the second medical image 540 has been captured. The reference image detection unit 310 may use a scheme, such as, for example, a Gabor wavelet scheme or a local binary pattern matching scheme to determine the similarity between each of the plurality of first medical images 550 and the second medical image 540.

According to the Gabor wavelet scheme, the reference image detection unit 310 filters the plurality of first medical images 550 and the second medical image 540 with several Gabor filters having different characteristics. The Gabor filters are linear filters having different frequencies, orientations, and they search for an edge by filtering a texture of an image. The reference image detection unit 310 compares results obtained by filtering each of the plurality of first medical images 550 and the second medical image 540 with each other to detect an image from among images 550 whose filtering result is most similar to the second medical image 540, and selects the image with the most similar result as the reference image 551.

According to the local binary pattern matching scheme, the reference image detection unit 310 selects a central pixel from each of the plurality of first medical images 550 and the second medical image 540 and binarizes differences between a pixel value of the central pixel and pixel values of surrounding pixels. The reference image detection unit 310 binarizes the pixel values of the surrounding pixels based on the pixel value of the central pixel and aligns the binarized pixel values in a pre-defined direction. The reference image detection unit 310 compares the aligned binarized pixel values in each of the plurality of first medical images 550 and the second medical image 540 with each other and detects an image having the most similar binarized pixel values as the reference image 551.

If images having different modalities are captured in similar breathing states, similarity between the images is larger than images captured in different breathing states. Thus, the reference image detection unit 310 may detect the reference image 551, which has been captured in the same or a very similar breathing state of the second medical image 540.

The landmark point extraction unit 320 extracts landmark points from the reference image 551 and the second medical image 540. Two or more landmark points may be extracted. A landmark point indicates a point used as a reference in image registration and may be extracted from anatomical objects shown in the reference image 551 and the second medical image 540. The anatomical objects include components of the subject, such as, for example, organs, blood vessels, lesions, bones, inter-organ interfaces. Since the reference image 551 and the second medical image 540 are captured in the same breathing state, it may be considered that the reference image 551 and the second medical image 540 have been captured in a state where shapes and locations of the anatomical objects are the same.

The landmark point extraction unit 320 may extract landmark points as described below.

A. A point at which an anatomical feature of an object is distinctively reflected is defined as a landmark point. For example, when an object from which landmark points are extracted is the liver, points at which blood vessels diverge in a blood structure inside the liver may be extracted as landmark points. As another example, when an object from which landmark points are extracted is the heart, an interface at which the right atrium and the left atrium divide and an interface at which the main vein and the outer wall of the heart meets may be extracted as landmark points.

B. The highest or lowest point of an object from which landmark points are extracted in a pre-defined coordinate system may also be designated as a landmark point.

C. Points for interpolating between the landmark points selected in A and B may be selected with a constant gap along the object. These points for interpolating may also be designated as landmark points.

When the designated landmark points are two-dimensional, the designated landmark points may be represented with coordinates of the x- and y-axes. When the designated landmark points are three-dimensional, the designated landmark points may be represented with coordinates of the x-, y-, and z-axes. Thus, when coordinates of three-dimensional landmark points are represented as vectors $x_0$, $x_1$, $x_{n-1}$ (n denotes the number of landmark points), the coordinates of the three-dimensional landmark points may be represented by Equation 1.

$$x_{i0} = [x_{i0}, y_{i0}, z_{i0}] \qquad (1)$$
$$x_{i1} = [x_{i1}, y_{i1}, z_{i1}]$$
$$\vdots$$
$$x_{in-1} = [x_{in-1}, y_{in-1}, z_{in-1}]$$

In Equation 1, i denotes landmark point coordinate information in an ith first medical image.

The first transform function calculation unit 330 calculates a first transform function for rotating, scaling, translating, or shearing any one of the reference image 551 and the second medical image 540 based on the other image by using the landmark points extracted by the landmark point extraction unit 320. The first transform function may be an affine transform function $T_{affine}$ calculated by an affine registration scheme. The affine transform function $T_{affine}$ may be calculated using an algorithm, such as, for example, an iterative closest point (ICP) algorithm. The ICP algorithm is an algorithm for minimizing the difference between two clouds of points, such as, the landmark points in the two images that correspond to each other.

Figure 7:
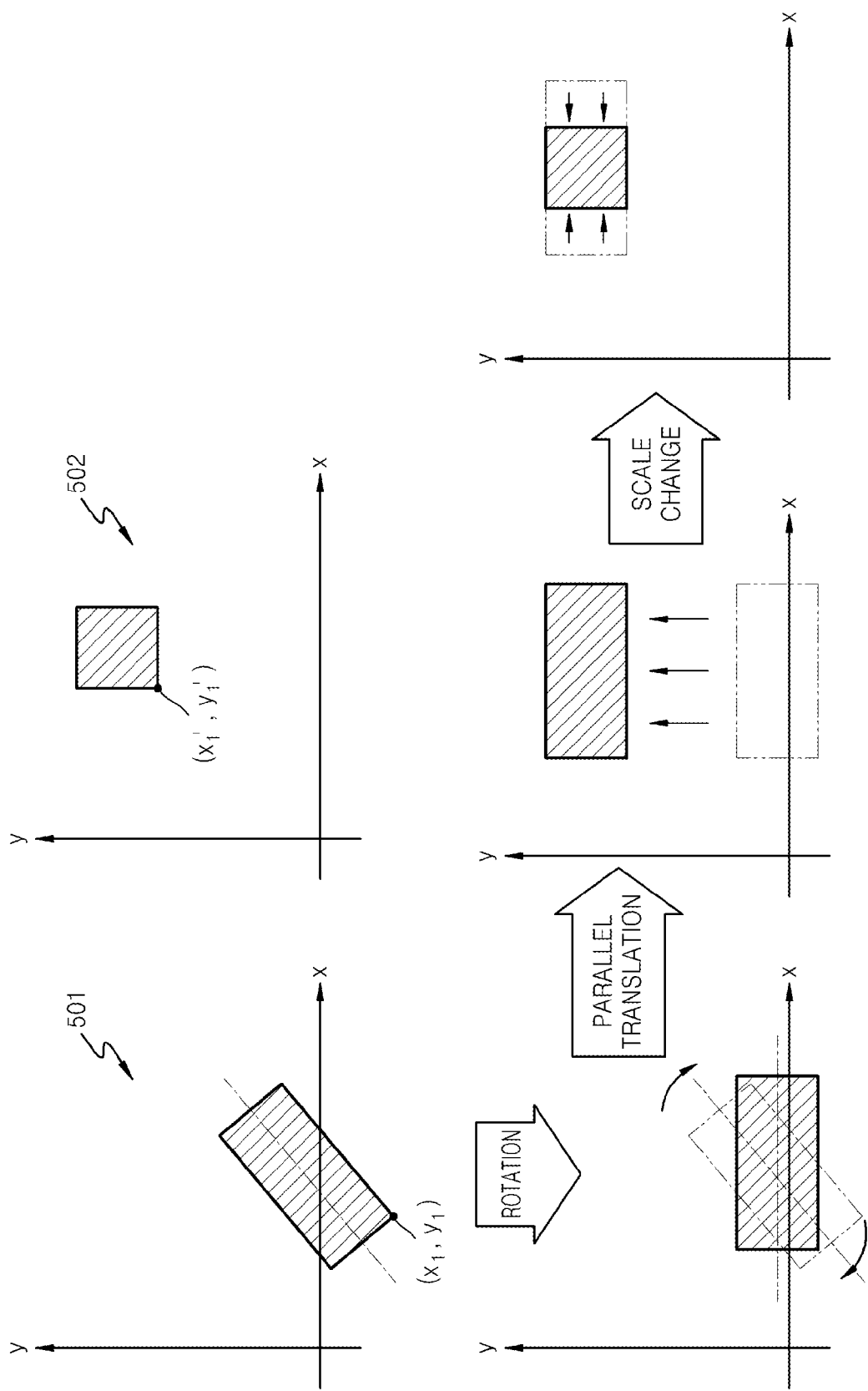
FIG. 7 diagram illustrating an example of a method of acquiring an affine transform function $T_{affine}$ from a two-dimensional image.

FIG. 7 illustrates a method of acquiring the affine transform function $T_{affine}$ from a two-dimensional image.

Reference numeral 501 denotes a state before the affine transform function $T_{affine}$ is applied, and reference numeral 502 denotes a state to be transformed by applying the affine transform function $T_{affine}$. Since an affine transform is one-to-one point correspondence, the affine transform function $T_{affine}$ may be determined by Equation 2.

$$\begin{bmatrix} x'_1 \\ y'_1 \end{bmatrix} = T_{affine} \begin{bmatrix} x_1 \\ y_1 \\ 1 \end{bmatrix} = \begin{bmatrix} a_1 & b_1 & c_1 \\ a_2 & b_2 & c_2 \end{bmatrix} \begin{bmatrix} x_1 \\ y_1 \\ 1 \end{bmatrix} \qquad (2)$$

The first coordinate transform unit 340 transforms or inverse transforms coordinates of the reference image 551 to coordinates of the second medical image 540 by using the first transform function. When it is assumed that a first point in the reference image 551 corresponds to a second point in the second medical image 540, the first point may be transformed or inverse transformed to the second point by the first coordinate transform unit 340.

FIG. 4 is a block diagram of the single-modality registration unit 2203. Referring to FIG. 4, the single-modality registration unit 2203 may include an object segmentation unit 410, a second transform function calculation unit 420, and a second coordinate transform unit 430.

The object segmentation unit 410 segments anatomical objects shown in the plurality of first medical images 550 from a background. Information about the anatomical objects to be segmented from the background may be provided in advance to the object segmentation unit 410. For example, blood vessel tissue has a darker brightness value than a background in an ultrasound medical image, and blood vessel brightness value information may be input to the object segmentation unit 410 in advance. As another example, information about the diaphragm that is a plane having a curvature of a predetermined value or less and information about the retrohepatic vena cava that is a blood vessel having a diameter of 10 mm or more may be input in advance to the object segmentation unit 410. Other information about anatomical objects may also be provided in advance to the object segmentation unit 410.

The object segmentation unit 410 may perform the segmentation by using schemes, such as, for example, a graph cut scheme or a Gaussian mixture model (GMM) scheme. According to the graph cut scheme, the object segmentation unit 410 gradually expands a region of a seed point of a background and a region of a seed point of an anatomical object by using a seed value of the background and a seed value of the anatomical object in the plurality of first medical images 550. The object segmentation unit 410 segments the anatomical object from the background by cutting a boundary region at which the seed point region of the background and the seed point region of the anatomical object expand and meet each other. According to the GMM scheme, the object segmentation unit 410 represents a color histogram of the plurality of first medical images 550 as a plurality of Gaussian distribution models. Thereafter, the object segmentation unit 410 segments anatomical objects by selecting a Gaussian distribution model of a preset band from the color histogram.

The second transform function calculation unit 420 calculates a second transform function for representing displacements and/or deformations of the anatomical objects within the first breathing period "t" by using the anatomical objects segmented from the reference image 551 and the other first medical images 552, 553, and 554. According to the second transform function, local deformation may be calculated.

The second transform function calculation unit 420 may calculate the second transform function according to a free-form deformation model scheme based on B-splines. Since the free-form deformation model scheme does not have to extract features and has a high degree of freedom as a method of deforming an object by moving a grid of control points forming B-splines, the free-form deformation model scheme is suitable to model complicated local deformation. The free-form deformation model scheme is disclosed in a non-patent document published by D. Rueckert et al., "Non-rigid registration using free-form deformations: Application to breast MR images," IEEE Trans. Medical Imaging, vol. 18, pp. 712-721, 1999, the entirely of which is incorporated by reference.

The second transform function calculation unit 420 generates gx×gy×gz control grids each consisting of control points ai, j, and k with an equivalent interval 6 from the plurality of first medical images 550. In this case, the second transform function for an arbitrary point (x, y, z) in the plurality of first medical images 550 may be represented by Equation 3.

$$T(x, y, z) = \sum_{p=0}^{3} \sum_{q=0}^{3} \sum_{r=0}^{3} B_p(u)B_q(v)B_r(w)\alpha_{i+p}. \quad (3)$$

In Equation 3, i=[x/gx]−1, j=[y/gy], k=[z/gz], u=x/gx−[x/gx], v=y/gy−[y/gy], and w=z/gz−[z/gz]. In addition, Bp, Bq, and Br are cubic B-spline base functions defined as Equation 4.

$$B_0(u)=(1-u^3)/6,$$

$$B_1(u)=(3u^3-6u^2+4)/6,$$

$$B_2(u)=(-3u^3+3u^2+3u+1)/6,$$

$$B_3(u)=u^3/6. \quad (4)$$

The second coordinate transform unit 430 transforms or inverse transforms coordinates of the reference image 551 to coordinates of the other first medical images 552, 553, and 554 by using the second transform function. When it is assumed that a third point in the reference image 551 corresponds to a fourth point in the first medical image 552, the third point may be transformed or inverse transformed to the fourth point by the second coordinate transform unit 430.

The object segmentation unit 410 may be omitted in the single-modality registration unit 2203. When the object segmentation unit 410 is omitted, the second transform function calculation unit 420 calculates the second transform function by not only considering coordinates of segmented anatomical objects but also considering coordinates of the whole image including a background. For example, when the probe 121 of the first medical device 120 minutely moves during the first breathing period "t," it captures displacements and deformations of the anatomical objects due to breathing. It also captures displacements and deformations of the background and the anatomical objects due to the movement of the probe 121 in the plurality of first medical images 550. In this case, the second transform function calculation unit 420 may compensate for the displacements and deformations due to the movement of the probe 121 in the whole displacement and deformation of the anatomical objects shown in the plurality of first medical images 550.

However, if the plurality of first medical images 550 are captured when the probe 121 is stationary, the second transform function is calculated by only considering the segmented anatomical objects, a computation amount may be reduced and the computation may be performed quickly.

Referring back to FIG. 2, the database construction unit 230 will now be described. The database construction unit 230 may include an object identifying unit 2301, an object modification unit 2302, and a registration image generation unit 2303. The database construction unit 230 generates a set 560 (refer to FIG. 5) of registration images between the plurality of first medical images 550 and the second medical image 540 for the first breathing period "t" by using the registration results in the multi-modality registration unit 2202 and the single-modality registration unit 2203. The database construction unit 230 stores the generated set 560 of registration images in the registration image database 2402.

The object identifying unit 2301 identifies shapes and locations of an organ and a lesion, which are shown in the second medical image 540, on coordinates of the reference image 551 by using the multi-modality registration result. The object identifying unit 2301 transforms coordinates of the organ and the lesion shown in the second medical image 540 to coordinates of the reference image 551 through the first coordinate transform unit 340.

The object modification unit 2302 estimates changes in shapes and locations of the organ and the lesion indentified on the coordinates of the reference image 551 for the first breathing period "t" by using the single-modality registration result. In other words, the object modification unit 2302 transforms coordinates of the organ and the lesion identified in the reference image 551 to coordinates of each of the other first medical images 552, 553, and 554 through the second coordinate transform unit 430. The object modification unit 2302 estimates displacements and deformations of the organ and the lesion for the first breathing period "t" through the transformed coordinates. The estimated result may be represented as a vector, and the vector is called a modification vector.

The registration image generation unit 2303 stores the plurality of first medical images 550 and modification vectors corresponding to the plurality of first medical images 550 in the registration image database 2402 by linking the plurality of first medical images 550 and the modification vectors to each other. In another example, when the plurality of first medical images 550 are stored in the raw image database 2401, the registration image generation unit 2303 may store the modification vectors in the registration image database 2402 and may link the modification vectors to physical or logical addresses of the plurality of first medical images 550 stored in the raw image database 2401. In this case, the plurality of first medical images 550 may not be stored in the registration image database 2402.

According to another non-exhaustive example, the object modification unit 2302 may modify anatomical information shown in the second medical image 540, e.g., shapes and locations of an organ and a lesion, to correspond to breathing states of the other first medical images 552, 553, and 554 by using modification vectors. The object modification unit 2302 modifies coordinates of the organ and the lesion shown in the second medical image 540 by using the modification vectors. The registration image generation unit 2303 adds the modified anatomical information to the plurality of first medical images 550. That is, the registration image generation unit 2303 stores the modified anatomical information, e.g., modified coordinates of the organ and the lesion, and the plurality of first medical images 550 in the registration image database 2402 by linking the modified anatomical information to the plurality of first medical images 550. As described above, the plurality of first medical images 550 may be or may not be stored in the registration image database 2402.

According to another non-exhaustive example, the object modification unit 2302 may modify the second medical image 540 by using modification vectors so that an organ and a lesion shown in the second medical image 540 correspond to breathing states of the plurality of first medical images 550. The modified second medical images are called modification images. The registration image generation unit 2303 stores the modification images and the plurality of first medical images 550 in the registration image database 2402 by respectively linking the modification images to the plurality of first medical images 550. As described above, the plurality of first medical images 550 may be or may not be stored in the registration image database 2402.

The real-time registration unit 250 acquires in real-time the third medical image 570 captured after the first breathing period "t" through the medical image acquisition unit 210. The real-time registration unit 250 detects an image 562 (refer to FIG. 5) corresponding to the third medical image 570 from the set 560 of registration images and outputs the detected image 562. The real-time registration unit 250 may include a registration image detection unit 2501 and an image output unit 2502.

The registration image detection unit 2501 detects the image 562 corresponding to the third medical image 570 from the registration image database 2402. The image 562 does not necessarily indicate a rendered image and may correspond to all or a portion of the data of a registration image. As described above, the image 562 may be any one of a modification vector, modified coordinates of an organ and a lesion, and a modification image, but is not limited thereto. It is assumed that the registration image detection unit 2501 detects the image 562 only with the plurality of first medical images 550 without determining information (modification vectors or modified coordinates of an organ and a lesion) linked to the plurality of first medical images 550 or determining similarities with the modification images. It will be understood by one of ordinary skill in the art that the image 562 may be detected by further considering the information (modification vectors or modified coordinates of an organ and a lesion) linked to the plurality of first medical images 550 or the modification images. The registration image detection unit 2501 detects the first medical image 552 having the highest similarity with the third medical image 570 from among the plurality of first medical images 550. The registration image detection unit 2501 may use the Gabor wavelet scheme or the local binary pattern matching scheme described above.

The image output unit 2502 outputs the image 562 detected by the registration image detection unit 2501. That is, the image output unit 2502 outputs information (a modification vector or modified coordinates of an organ and a lesion) or a modification image stored by being linked to the first medical image 552, which has the highest similarity with the third medical image 570. When the modification vector or modified coordinates of an organ and a lesion are stored in the registration image database 2402 by being linked to plurality of first medical images 550, the image output unit 2502 may generate a modification image based on the modification vector or modified coordinates of an organ and a lesion and may output the modification image.

Figure 5:
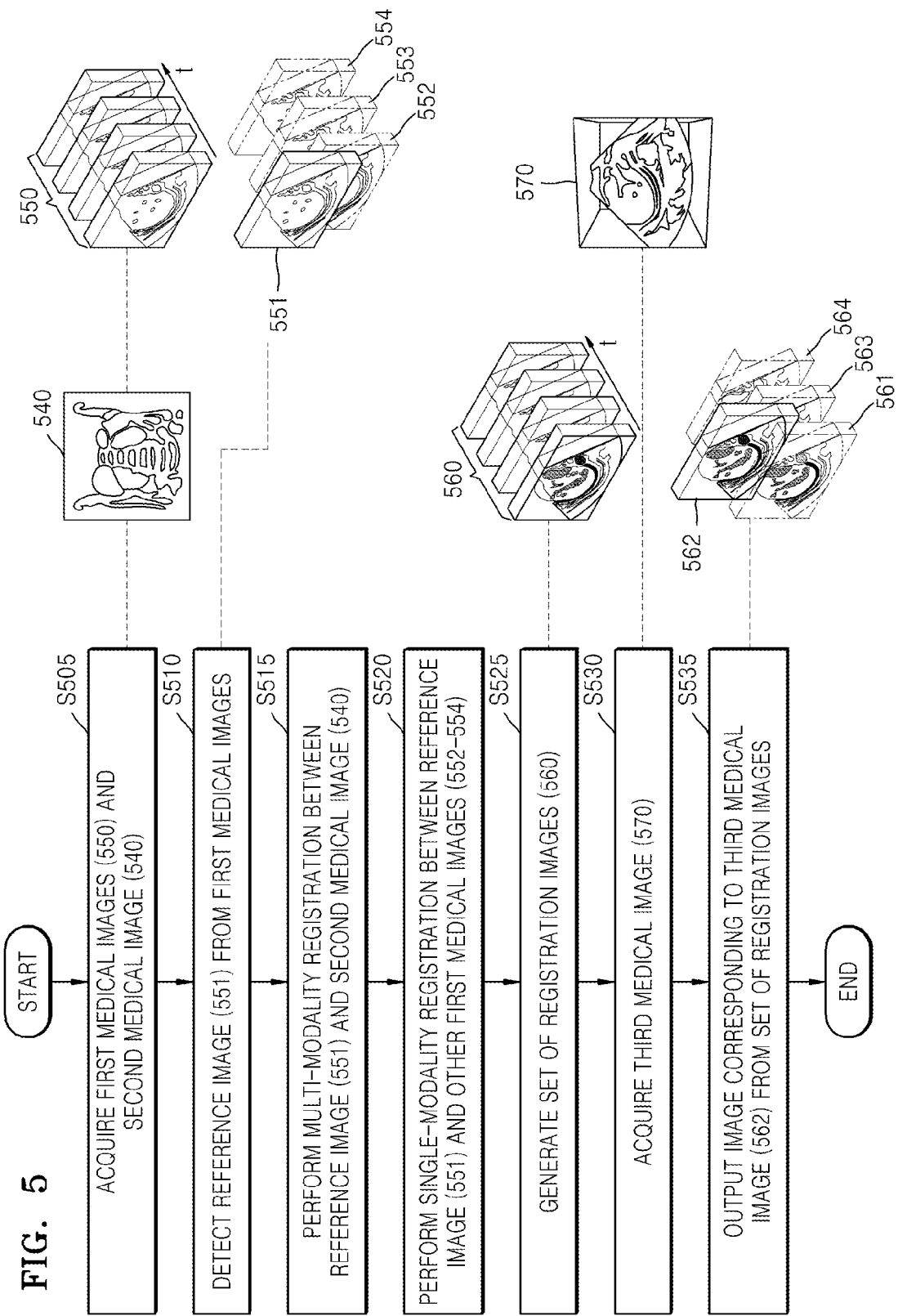
FIG. 5 is a diagram illustrating an example of a medical image registration method.

According to the example of FIG. 5, the set 560 of registration images is a fusion image, but this is for convenience of description, and as described above, the current examples are not limited thereto.

The control unit 260 controls the medical image acquisition unit 210, the initial registration unit 220, the database construction unit 230, the storage unit 240, and the real-time registration unit 250. When registration between images acquired by the first interface 2101 is performed, the control unit 260 controls the single-modality registration unit 2203 to perform the registration, and when registration between images acquired by the first interface 2101 and the second interface 2102 is performed, the control unit 260 controls the multi-modality registration unit 2202 to perform the registration. In addition, when registration between a set of registration images stored in the registration image database 2402 and the images acquired by the first interface 2101 is performed, the control unit 260 controls the real-time registration unit 250 to perform the registration.

The control unit 260 may provide a user interface (not shown) for receiving a selection of a registration mode. The registration mode includes an initial registration mode for generating the set 560 of registration images and a real-time registration mode for registration between the set 560 of registration images and the third medical image 570. A user may select the initial registration mode before a medical procedure and may select the real-time registration mode during the medical procedure.

The control unit 260 may be implemented by an array of a plurality of logic gates or a combination of a general-use microprocessor and a memory in which programs executable by the general-use microprocessor are stored. In addition, it will be understood by one of ordinary skill in the art that the control unit 260 may be implemented by other forms of hardware. Only hardware components related to the examples described above have been described with reference to FIGS. 1 to 4. However, it will be understood by one of ordinary skill in the art that other general-use hardware components may be further included in addition to the hardware components shown in FIGS. 1 to 4.

FIG. 5 is a diagram illustrating an example of a medical image registration method. The operations in FIG. 5 may be performed in the sequence and manner as shown, although the order of some operations may be changed or some of the operations omitted without departing from the spirit and scope of the illustrative examples described. Many of the operations shown in FIG. 5 may be performed in parallel or concurrently. The medical image registration method shown in FIG. 5 includes operations sequentially processed by the medical image registration apparatus 130 of FIG. 1 or 200 of FIG. 2. The description of medical image registration apparatuses of FIGS. 1-4 is also applicable to FIG. 5, and thus will not be repeated here.

In S505, the medical image registration apparatus 130 or 200 acquires the plurality of first medical images 550 captured for the first breathing period "t" of the subject and the second medical image 540 having a different modality from the plurality of first medical images 550.

In S510, the medical image registration apparatus 130 or 200 detects the reference image 551 based on similarities between the plurality of first medical images 550 and the second medical image 540. The medical image registration apparatus 130 or 200 detects an image, which has been captured in a breathing state most similar to a breathing state in which the second medical image 540 has been captured from among the plurality of first medical images 550, as the reference image 551.

In S515, the medical image registration apparatus 130 or 200 registers the reference image 551 and the second medical image 540. The medical image registration apparatus 130 or 200 performs rigid registration or affine registration of the reference image 551 and the second medical image 540. The medical image registration apparatus 130 or 200 extracts landmark points from the reference image 551 and the second medical image 540. Thereafter, the medical image registration apparatus 130 or 200 rotates, scales, translates, or shears any one of the reference image 551 and the second medical image 540 based on the other image by using the extracted landmark points.

In S520, the medical image registration apparatus 130 or 200 registers each of the other first medical images 552, 553, and 554 acquired in different breathing states from the reference image 551 and the reference image 551. The medical image registration apparatus 130 or 200 performs non-rigid registration of the reference image 551 and the other first medical images 552, 553, and 554. The medical image registration apparatus 130 or 200 may estimate displacements and deformations of organs and lesions for the first breathing period "t" by using brightness information and gradient information between the reference image 551 and each of the other first medical images 552, 553, and 554.

In S525, the medical image registration apparatus 130 or 200 generates the set 560 of registration images for the first breathing period "t" by using the registration results in operations S515 and S520. The medical image registration apparatus 130 or 200 may modify anatomical information shown in the second medical image 540 to correspond to breathing states of the other first medical images 552, 553, and 554 by using the registration result in operation S520. The medical image registration apparatus 130 or 200 may add the modified anatomical information, e.g., modified coordinates of organs and lesions, to the other first medical images 552, 553, and 554.

In S530, the medical image registration apparatus 130 or 200 acquires the third medical image 570 captured in real-time after the first breathing period t. In S535 an image is outputted corresponding to the third medical image 562 from a set of registration images.

The medical image registration apparatus 130 or 200 detects the image 562 corresponding to the third medical image 570 from the set 560 of registration images and outputs the detected image 562. The medical image registration apparatus 130 or 200 detects the first medical image 552 having the highest similarity with the third medical image 570 from among the plurality of first medical images 550. Thereafter, the medical image registration apparatus 130 or 200 outputs anatomical information added in the image 562 corresponding to the third medical image 570 from among the set 560 of registration images.

Figure 6A:
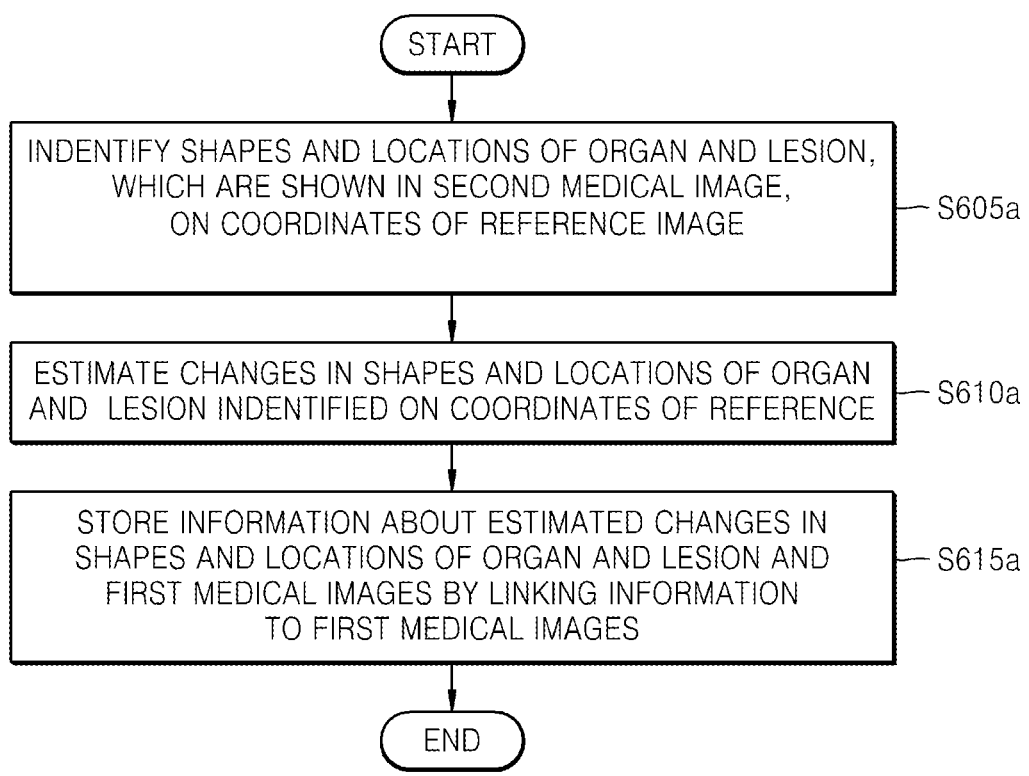
FIG. 6A is a diagram illustrating an example of an operation of generating a set of registration images in the medical image registration method of FIG. 5.

FIG. 6A is a diagram illustrating an example of an operation of generating the set 560 of registration images in the medical image registration method of FIG. 5. The operations in FIG. 6A may be performed in the sequence and manner as shown, although the order of some operations may be changed or some of the operations omitted without departing from the spirit and scope of the illustrative examples described. Many of the operations shown in FIG. 6A may be performed in parallel or concurrently. The description of medical image registration apparatuses and methods of FIGS. 1-5 is also applicable to FIG. 6A, and thus will not be repeated here.

In S605a, the medical image registration apparatus 130 or 200 identifies shapes and locations of an organ and a lesion, which are shown in the second medical image 540, on coordinates of the reference image 551 by using the registration result of operation S515.

In S610a, the medical image registration apparatus 130 or 200 estimates changes in shapes and locations of the organ and the lesion indentified on the coordinates of the reference image 551 for the first breathing period "t" by using the registration result of operation S520.

In S615a, the medical image registration apparatus 130 or 200 stores information about the changes in the shapes and locations of the organ and the lesion, e.g., modification vectors, and the plurality of first medical images 550 by linking the plurality of first medical images 550 and the modification vectors to each other.

FIG. 6B is a diagram illustrating another example of an operation of generating the set 560 of registration images in the medical image registration method of FIG. 5. The operations in FIG. 6B may be performed in the sequence and manner as shown, although the order of some operations may be changed or some of the operations omitted without departing from the spirit and scope of the illustrative examples described. Many of the operations shown in FIG. 6B may be performed in parallel or concurrently. The description of medical image registration apparatuses and methods of FIGS. 1-6A is also applicable to FIG. 6B, and thus will not be repeated here.

In operation S605b, the medical image registration apparatus 130 or 200 identifies shapes and locations of an organ and a lesion, which are shown in the second medical image 540, on coordinates of the reference image 551 by using the registration result of operation S515.

In operation S610b, the medical image registration apparatus 130 or 200 estimates changes in shapes and locations of the organ and the lesion indentified on the coordinates of the reference image 551 for the first breathing period "t" by using the registration result of operation S520.

In operation S615b, the medical image registration apparatus 130 or 200 generates modification images by modifying the organ and the lesion shown in the second medical image 540 by using information about the estimated changes in the shapes and locations of the organ and the lesion, e.g., modification vectors.

In operation S620b, the medical image registration apparatus 130 or 200 stores the modification images and their corresponding first medical images 550 by linking the modification images to the corresponding first medical images 550.

As described above, when a second medical image having a different modality from first medical images is registered with the first medical images, multi-modality registration and single-modality registration are identified and are performed in phases, and thus, a computation amount necessary for the registration may be reduced, and an accuracy of the registration may be improved.

The methods described above can be written as a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device that is capable of providing instructions or data to or being interpreted by the processing device. The software also may be distributed over network coupled computer systems so that the software is stored and executed in a distributed fashion. In particular, the software and data may be stored by one or more non-transitory computer readable recording mediums. The non-transitory computer readable recording medium may include any data storage device that can store data that can be thereafter read by a computer system or processing device. Examples of the non-transitory computer readable recording medium include read-only memory (ROM), random-access memory (RAM), Compact Disc Read-only Memory (CD-ROMs), magnetic tapes, USBs, floppy disks, hard disks, optical recording media (e.g., CD-ROMs, or DVDs), and PC interfaces (e.g., PCI, PCI-express, WiFi, etc.). In addition, functional programs, codes, and code segments for accomplishing the example disclosed herein can be construed by programmers skilled in the art based on the flow diagrams and block diagrams of the figures and their corresponding descriptions as provided herein.

The apparatuses and units described herein may be implemented using hardware components. The hardware components may include, for example, controllers, sensors, processors, generators, drivers, and other equivalent electronic components. The hardware components may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The hardware components may run an operating system (OS) and one or more software applications that run on the OS. The hardware components also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a hardware component may include multiple processors or a processor and a controller. In addition, different processing configurations are possible, such a parallel processors.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An image registration method comprising:
performing, at a processor, multi-modality registration of a reference image from first images captured during a first breathing period and a second image;
performing, at the processor, single-modality registration of the reference image and each of the others of the first images;
generating registration images for the first breathing period responsive to the performed multi-modality registration and the performed single-modality registration;
acquiring a third image captured after the first breathing period; and
detecting an image corresponding to the third image from among the registration images.

2. The image registration method of claim 1, further comprising outputting the detected image.

3. The image registration method of claim 1, wherein the generating of the registration images comprises:
modifying anatomical information included in the second image to correspond to different breathing states of the other first images based on the single-modality registration; and
adding the modified anatomical information to the other first images.

4. The image registration method of claim 2, wherein:
the detecting of the image corresponding to the third image comprises detecting an image having the highest similarity with the third image from the first images; and
outputting the detected image comprises outputting anatomical information added in the registration image corresponding to the detected image from the first images.

5. The image registration method of claim 1, wherein:
the performing of the multi-modality registration comprises performing rigid registration or affine registration of the reference image and the second image, and the performing of the single-modality registration comprises performing non-rigid registration of the reference image and the other first images.

6. The image registration method of claim 1, wherein the performing of the multi-modality registration comprises:
extracting landmark points from each of the reference image and the second image; and
rotating, scaling, translating, or shearing any one of the reference image and the second image based on an other one of the reference image and the second image and the extracted landmark points.

7. The image registration method of claim 1, wherein the performing of the single-modality registration comprises estimating a displacement and a deformation of an organ or a lesion for the first breathing period by using brightness information and gradient information between the reference image and each of the other first images.

8. The image registration method of claim 1, wherein the reference image is an image that has been captured in a breathing state most similar to a breathing state in which the second image has been captured.

9. The image registration method of claim 1, wherein the generating of the registration images comprises:
identifying a shape and a location of an organ or a lesion, which are shown in the second image, on coordinates of the reference image by using the multi-modality registration; and
estimating changes in the shape and the location of the organ or the lesion identified on the coordinates of the reference image with each of the other first images by using the single-modality registration.

10. The image registration method of claim 9, further comprises storing information about the estimated changes in the shape and location of the organ or the lesion by linking the information to the first images.

11. The image registration method of claim 9, wherein the generating of the registration images further comprises:
generating modification images by modifying the organ or the lesion shown in the second image to correspond to the first images by using the estimated shape and location of the organ or the lesion; and
storing the first images and the modification images by linking the other first images to the modification images.

12. A image registration apparatus comprising:
a processor configured to perform multi-modality registration of a reference image from first images captured during a first breathing period and a second image,
perform single-modality registration of the reference image and each of the others of the first images,
generate registration images for the first breathing period responsive to the performed multi-modality registration and the performed single-modality registration,
acquire a third image captured after the first breathing period, and
detect an image corresponding to the third image from among the registration images.

13. The image registration apparatus of claim 12, wherein the processor further modifies anatomical information shown in the second image to correspond to different breathing states of the other first images based on the single-modality registration and adds the modified anatomical information to the other first images.

14. The image registration apparatus of claim 13, wherein the processor further detects an image having the highest similarity with the third image from the first images and outputs anatomical information added in the image having the highest similarity with the third image from the registration images.

15. The image registration apparatus of claim 12, wherein the processor further performs multi-modality registration by performing rigid registration or affine registration of the reference image and the second image, and
performs single-modality registration by performing non-rigid registration of the reference image and the other first images.

16. The image registration apparatus of claim 12, wherein the processor further extracts landmark points from each of the reference image and the second image, and rotates, scales, translates, or shears any one of the reference image and the second image based on the other image and the extracted landmark points.

17. The image registration apparatus of claim 12, wherein the processor further estimates a displacement and a deformation of an organ or a lesion for the first breathing period by using brightness information and gradient information between the reference image and each of the other first images.

18. The image registration apparatus of claim 12, wherein the processor further detects the reference image as an image that, has been captured in a breathing state most similar to a breathing state in which the second image has been captured.

19. The image registration apparatus of claim 12, wherein the processor further identifies a shape and a location of an organ or a lesion shown in the second image based on coordinates of the reference image responsive to the multi-modality registration and estimates changes in the shape and the location of the organ or the lesion identified based on the coordinates of the reference image with each of the other first images responsive to the single-modality registration.

20. The image registration apparatus of claim 19, wherein the processor further stores information about the estimated changes in the shape and the location of the organ or the lesion by linking the information to the first images.

21. The image registration apparatus of claim 19, wherein the processor further generates modification images by modifying the organ and the lesion shown in the second image to correspond to the first images by using the estimated shape and the location of the organ or the lesion and to store the first images and the modification images by linking the other first images to the modification images.

22. The image registration apparatus of claim 12, wherein the third image is acquired in real-time.

* * * * *